Figure 1:
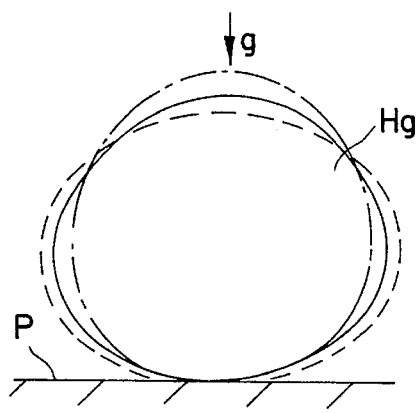

United States Patent [19]

Inguaggiato

[11] Patent Number: 5,533,520
[45] Date of Patent: Jul. 9, 1996

[54] ACTIVITY SENSOR, PARTICULARLY FOR HEART PACEMAKERS

[75] Inventor: Bruno Inguaggiato, Milan, Italy

[73] Assignee: Sorin Biomedica, S.p.A., Saluggia, Italy

[21] Appl. No.: 501,248

[22] Filed: Jul. 10, 1995

Related U.S. Application Data

[63] Continuation of Ser. No. 119,798, Sep. 10, 1993, abandoned, which is a continuation of Ser. No. 848,387, Mar. 9, 1992, abandoned, which is a continuation of Ser. No. 473,864, Feb. 5, 1990, abandoned.

[30] Foreign Application Priority Data

Feb. 13, 1989 [IT] Italy .................................. 67085/89

[51] Int. Cl.$^6$ .................................................. A61B 5/10
[52] U.S. Cl. .................. 128/782; 607/19; 200/61.45 R; 200/185; 200/220
[58] Field of Search .............................. 128/782; 607/17, 607/19, 48, 49; 200/61.45 R, 61.52, 185, 199–201, 214, 220, DIG. 2, DIG. 9, DIG. 18, DIG. 20, DIG. 30

[56] References Cited

U.S. PATENT DOCUMENTS

| 3,083,712 | 4/1963 | Keegan, Jr. ........................ 128/423 W |
| 3,539,740 | 11/1978 | Isenor et al. ...................... 200/61.45 R |
| 3,935,669 | 2/1976 | Potrzuski et al. ................ 200/61.45 R |

OTHER PUBLICATIONS

Matula et al "A New Mechanical Sensor for the Detection of Body Activity & Posture Suitable for Rate Responsive Pacing; Pace"; vol 10; Sep. 1989.

*Primary Examiner*—David M. Shay
*Attorney, Agent, or Firm*—Robert D Schaffer; Rogers and Wells

[57] ABSTRACT

The sensor is intended preferably for use in conjunction with a heart pacemaker whose stimulation rate is variable in dependence on the physical activity of the wearer. The sensor includes a mass of mercury which, in use, can assume a shape determined by the gravitational force and variable as a result of the forces applied to the mass due to movement. Detector means sensitive to the variations in shape generate signals which can be used as activity monitoring signals.

10 Claims, 1 Drawing Sheet

ACTIVITY SENSOR, PARTICULARLY FOR HEART PACEMAKERS

This application is a continuation of U.S. patent application Ser. No. 08/119,798, filed Sept. 10, 1993, which is a continuation of Ser. No. 07/848,387 filed on Mar. 9, 1992, which is a continuation of U.S. patent application Ser. No. 07/473,864 filed Feb. 5, 1990, now abandoned.

DESCRIPTION

The present invention relates to activity sensors and has been developed with particular attention to its possible use in conjunction with a heart pacemaker of the type currently termed "rate adaptive". In other words, this is a pacemaker in which the frequency of the stimulation pulses applied to the wearer's heart varies in dependence on a signal indicative of the physical activity of the wearer at the time.

Heart pacemakers of this type are widely known in the art.

For example, U.S. Pat. No. 4,140,132 describes the use, in an artificial implantable member such as a heart pacemaker, of an accelerometer constituted in principle by a piezoelectric crystal mechanically linked to a mass in order to produce an alternating voltage in dependence on the forces applied to the pacemaker.

The response of such a sensor, however, depends on the direction of the force and, in practice, this restricts the pacemaker to a fixed location relative to the wearer's body, in order primarily to detect variations in the gravitational acceleration resulting, for example, from the wearer walking or running.

In European Patent Application No. 0 259 658, the signal of an accelerometer constituted by a piezolectric, piezoresistive or piezocapacative mechanical-electrical, semiconductor-type transducer which can be integrated in a silicon chip with a circuit for analysing the signal is identified as useful for piloting the frequency of a pacemaker.

In this case also, it can be seen that, as in U.S. Pat. No. 4,140,132, the accelerometer described is more developed technologically and more responsive than the current state of the art. However, it retains the directional characteristic which makes it unacceptable for installation in a pacemaker for implantation in the human body, for which no orientation can be predetermined absolutely since the container may rotate through 360° about an axis parallel to the ground, whilst in a standing man the surface of the container may be inclined to the vertical (the gravitational axis) at an angle which can vary between −10° and +40°.

U.S. Pat. No. 4,428,378 describes another activity sensor which uses a piezoelectric crystal. In this case, the problem of the detection being directional is resolved by considering only the fairly-high-frequency components of the external forces transmitted to the pacemaker from any source. This crystal is simply glued to the wall of the pacemaker casing and therefore does not respond to gravitational accelerations or decelerations (which are obviously directional) but can detect vibrations resulting from the impact of the wearer's foot on the ground, tapping on the wearer's chest, etc.

Finally, the study presented by Markus Matula and others to the 6th Cardiostim 88 in Monaco, entitled "A New Mechanical Sensor for the Detection of Body Activity and Posture Suitable for Rate-Responsive Pacing" and published in PACE, June 88, Vol. 18, No. 6, should be mentioned. This study describes a pacemaker piloted by a sensor constituted by a multicontact tilt switch which contains a mass of mercury and discriminates between rest and low and high activity from from the movement of the mercury which comes into contact with the numerous contacts so as to open or close them. The number of transitions reported, which varies from a minimum of 20 to more than 100 every 3 seconds according to the level of activity, clearly shows that the system responds to frequencies of between 5–7 Hz and 30 Hz, making it insensitive to the gravitational accelerations which are generated, for example, during walking and have a maximum frequency of approximately 4 Hz.

A somewhat similar arrangement is disclosed also in U.S. Pat. No. 4,771,780.

Essentially, the results achieved by the sensors of this latter type are comparable to that of the sensor described in U.S. Pat. No. 4,428,378, although with different technology.

As with other solutions known in the art, therefore, the solutions described in these previous patents are not entirely satisfactory from the point of view of use because their detection is directional, because they are insensitive to very low-frequency forces of the order of one Hz (which are the most important for identifying the actual physical activity of the wearer) and/or because the accentuated sensitivity of the components to higher-frequency forces makes the sensor (and hence the pacemaker connected thereto) sensitive to external influences (vibrations, accidental knocks of the wearer's body) which do not correspond to actual physical activity and therefore do not necessitate a variation of the stimulation rate.

The object of the present invention, therefore, is to provide an activity sensor in which the aforesaid disadvantages are radically eliminated.

According to the present invention, this object is achieved by virtue of an activity sensor, particularly for a heart pacemaker, characterised in that it includes:

a mass of mercury (for example, of the order of 20–40 micrograms and preferably approximately 30 micrograms) which, in use, can assume a given shape determined by the gravitational force and variable as a result of forces applied to the mass due to movement, and detector means which are sensitive to the variations of the predetermined shape and can generate a signal indicative of the variations, the signal constituting an activity monitoring signal.

Advantageous characteristics of the solution according to the present invention are recited in the claims which follow.

In other words, the present invention provides an accelerometer which can be implanted and has a response that is independent of the axis of the active force and of the direction of movement in all three dimensions. In other words, this is a non-piezoelectric sensor which can respond to the gravitational accelerations and decelerations occurring when a man is walking or running completely independently of the direction in which the gravitational force acts relative to the geometry of the sensor.

Figure 4:
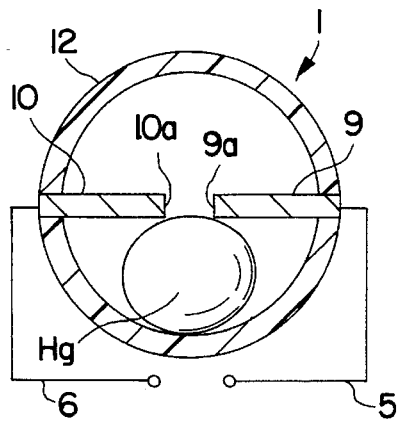
Figure 2:
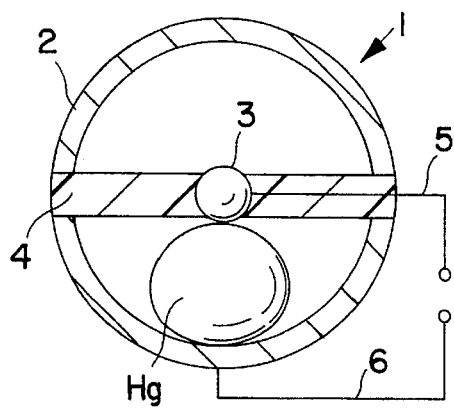
Figure 5:
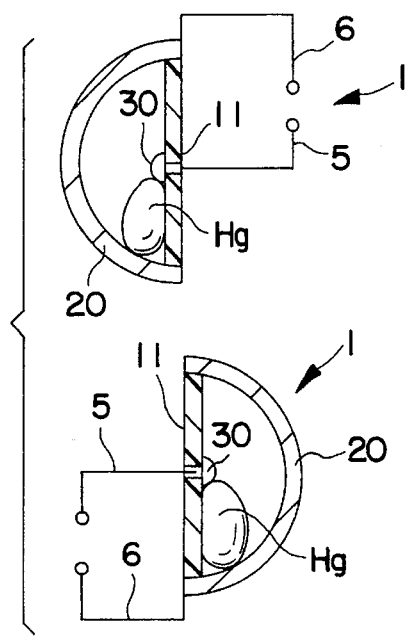
Figure 3:
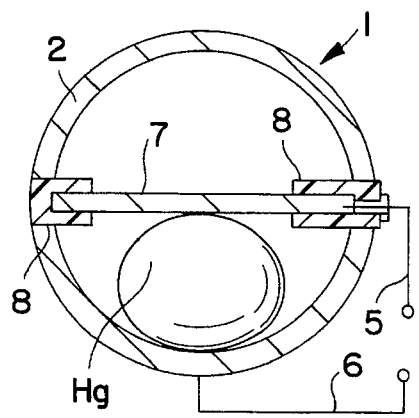
Figure 6:
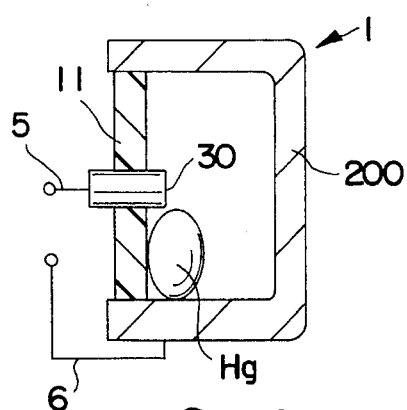

The invention will now be described, purely by way of non-limiting example, with reference to the appended drawings, in which:

FIG. 1 shows schematically the general operating principle of the sensor according to the invention, FIG. 2 shows a first embodiment of the sensor according to the invention, FIG. 3 shows a second possible embodiment of the sensor according to the invention, FIG. 4 shoes a third possible embodiment of the sensor according to the invention, FIG. 5 shows a fourth possible embodiment of the sensor according to the invention, and FIG. 6 shows yet another possible embodiment of the sensor according to the invention.

With reference to FIG. 1, a mass (drop) of mercury comprising, for example, 20–40 micrograms, preferably approximately 30 micrograms, of mercury is generally indicated Hg. Such a mass of mercury has a diameter of the order of about 3 mm.

When it is resting on a flat surface, generally indicated P, the mass Hg tends to assume the shape of an ellipsoid of rotation with its minor axis in the direction of the gravitational force g.

In the presence of external forces (which may theoretically be considered as disturbances $\pm\Delta g$ of the gravitational force), the mass of mercury Hg is deformed and assumes ellipsoidal shapes which are more squashed or rounded, or more elongate or slender according to the direction of the force, as shown schematically in broken outline and in chain outline in FIG. 1.

In general, in the presence of a force due to an upward movement, such as that which occurs during the first part of a step taken by a person in whom the sensor according to the invention is fitted, there will be a change in the shape of the mass Hg corresponding to a squashing of the ellipsoid (the broken line of FIG. 1). The mass will then tend to return spontaneously and elastically to its starting shape, possibly extending upwards (the chain line of FIG. 1) as a result of a downward movement of the wearer's body.

The Applicant has found that with the quantity of mercury indicated above and the consequent diameter referred to above, the changes in the shape of the mass of mercury as a result of movements with frequencies of the order of one Hz, such as those resulting from walking or running movements of a normal adult, are clearly detectable.

In general, a reduction in the mass of mercury Hg (with a consequent reduction in its dimensions) corresponds to an increase in the frequency of the detectable forces due to movement, but this does not appear to correspond to a desirable result in the context of the preferred application for the reasons clearly explained in the introduction to the present description.

In the schematic view of FIG. 2, in which an activity sensor according to the invention is generally indicated 1, a spherical casing of electrically-conductive material with a diameter of the order of 5–10 mm, preferably 6–7 mm, is indicated 2 and contains a mass of mercury Hg with the aforementioned characteristics.

The dimensions of the casing are therefore such as to enable it to be implanted easily in the body of a wearer of a heart pacemaker, to which the sensor 1 can be connected as an activity sensor.

The criteria for the connection of an activity sensor to a heart pacemaker can be considered as widely known in the art and do not therefore require a specific description here.

As regards the selection of the material constituting the casing 2, it is possible, for example, to use stainless steel or any other electrically-conductive material with good characteristics of chemical inertness and biocompatibility so as not to give rise to particular problems when implanted in the wearer's body.

A small sphere of electrically-conductive material with a diameter of the order of 0.15 mm, for example, is situated in the centre of the spherical casing 2.

The sphere 3 is kept in a central position in the casing 2 by a support 4 constituted by a crossbar of electrically-insulating material which extends between two diametrally-opposed points of the body of the casing 2 and passes through or surrounds the sphere 3.

For reasons which will become clearer from the following description, the diameter of the support 4 is preferably as small as possible, and it should be understood that, for clarity of illustration, the representation of this element in FIG. 1 is definitely enlarged in comparison with the other elements shown.

A conductive filament 5 in electrical contact with the sphere 3 extends through one of the arms of the support 4 and projects from the casing 2. A further electrical contact 6 is connected to the casing (at any point on its surface).

The diameters of the casing 2 and the sphere 3 are selected in coordination with the diameter of the mass of mercury Hg so that, under normal conditions, in the absence of external forces (that is, when the sensor 1 is "off" with the mass of mercury Hg subject only to gravitational acceleration) the mass of mercury Hg touches or bathes the sphere 3 and makes an electrical contact between the wires 5 and 6.

This electrical contact may be broken because of the squashing of the mass of mercury Hg resulting from a force due to an upward movement (the broken line of FIG. 1). The breaking of the electrical connection between the electrodes 5 and 6 is detectable (by known means) and in fact corresponds to the emission of a signal indicative of the change in shape of the mass of mercury Hg and hence of an activity monitoring signal.

The general spherical symmetry of the sensor 1 means that it can operate in practically the same manner whatever its position of fitting.

In any event, the mass of mercury Hg will actually tend to move to the lowest region of the casing 2, making or breaking the electrical connection between the casing 2 and the central sphere 3 in dependence on the forces applied to the sensor 1 due to movement.

These forces obviously correspond to movements (and hence to the physical activity) of the person in whom the sensor is fitted.

The sensor according to the invention can therefore completely eliminate the disadvantage of directional detection present in some sensors of the prior art.

Similarly, the frequency range of the forces to which the sensor is sensitive can be determined clearly by the selection of the size of the mass of mercury Hg, so that this range corresponds with the frequency range of the forces typical of a physical activity such as walking or running.

Naturally, the solution of FIG. 2 can have a very large number of possible variants, particularly as regards:

the type of detector means which are sensitive to the changes in the shape of the mass of mercury Hg (in the present description, reference has been made only to electrical detector means: however, quite clearly and therefore certainly within the scope of the present invention—the changes in the shape of the mass of mercury Hg can also be detected by different means, for example, optical means);

the nature of the detection, which may be of the "on-off" type (contact open/contact closed) as in the embodiment described above, or continuous as will be described further below with reference to FIG. 3, and the selection of the shape of the casing 2 which must in any event contain the mass of mercury Hg but may be modified, though preferably to a shape which, at least locally, has a certain symmetry of rotation about a certain axis: this selection ensures that the sensor is in fact unaffected by rotations about the axis of symmetry.

Some possible variants of the solution of FIG. 2 will be described below with reference to FIGS. 3 to 6.

In all these drawings, the reference numerals and symbols used above have been used to indicate parts identical or functionally equivalent to those described above.

For example, in the variant illustrated in FIG. 3, the sphere 3 has been eliminated and replaced by an element of resistive material (that is, an element which is at least partially electrically conductive) mounted in the casing 1 with the interposition of the insulating bushes 8 in positions approximately corresponding to that of the support 4 in FIG. 2.

The mass of mercury Hg bathes the resistive element 7 so as to make an electrical contact with the casing 6. The extent of the region of the element 7 bathed by the mass of mercury Hg, that is, the part of the surface of the element 7 which is in electrical contact with the casing 2, varies in dependence on the deformation of the drop of mercury Hg.

This means that the forces applied to the sensor 1 as whole due to movement vary the ohmic resistance detectable between the contact wire 5 which is connected to one of the ends of the resistive element 7) and the contact wire 6 (which again in this case is connected to the conductive casing 2).

Unlike the "on/off" detection achieved in the solution of FIG. 2, the detection in the solution of FIG. 3 is continuous in the sense that the resistance signal detectable between the wires 5 and 6 varies continuously in dependence on the change in the shape of the mass of mercury Hg.

In the embodiment of FIG. 4, the casing, indicated 12, is made of electrically-insulating material.

Two strips or electrical contacts 9, 10 project into the casing and are connected to the conductors 5 and 6 respectively.

The parts 9 and 10 are aligned diametrally in the casing 12 so that their free ends 9a, 10a are separated by a selected distance approximately equal to the diameter of the sphere 3 of the embodiment of FIG. 2.

In this case, the mass of mercury Hg bathes the two free ends 9a, 10a under normal conditions so as to afford electrical continuity between the conductors 5 and 6. When the mass of mercury Hg is squashed as a result of a force due to an upward movement, it tends to become separated from both the free ends 9a, 10a (or at least from one of them) so as to break the connection. In this case also, a signal (of the on/off type) indicative of the movement of the sensor can be detected between the conductors 5 and 6.

To a certain extent, the further variant of FIG. 5 may be seen as resulting from the division of the sensor shown in FIG. 2 into two specular parts.

In this case, the outer casing 2 of electrically-conductive material is divided into two hemispherical half-shells closed by flat insulating walls 11 and mounted with their spherical surfaces facing towards two opposite half-spaces.

A hemispherical button or stud 30 comparable in theory to half of the sphere 3 of FIG. 2 is mounted in the centre of the flat wall of each half-shell 20.

A respective mass of mercury Hg is situated in each of the half-shells 20 and can make an electrical connection between the button 30 (which is connected to the conductor 5) and the casing 20 (which is connected to the conductor 6), the connection being broken in the presence of a deformation corresponding to a squashing of the mass Hg.

Each of the half-shells can perform its detection function throughout the range of positions of use in which the mass of mercury Hg bears at least partly against the spherical wall of conductive material.

When the mass Hg ends up against the flat wall 31 as a result of a movement of the wearer, the detection is interrupted. The relative arrangement of the two half-shells, however, means that, when detection is not possible with one of the half-shells, it will certainly be possible with the other half-shell.

The detection of the sensor as a whole is therefore ensured in any case.

Naturally, the general principle represented by FIG. 5 may be developed further and extended to an even greater number of part-shells with even smaller portions of the spherical surface, for example, with the use of three or more sensors arranged so as to ensure complete coverage of the space and each operating in a certain range of orientations of the wearer. It will be understood that these further developments are definitely within the scope of the present invention.

Moreover, with reference to FIG. 6, a further variant is shown, in which the spherical half-shell 20 of FIG. 5 is replace by a cylindrical or cup-shaped casing 200 so as to retain characteristics of rotational symmetry about the principle axis of the cylindrical casing.

What is claimed is:

1. A sensor for detecting activity of a patient wearing a pacemaker, comprising:

a) a mass of mercury positioned in an initial location, wherein said mass of mercury has an initial shape due to gravitation acting thereon, wherein said mass of mercury is in the range of about 20 micrograms to about 40 micrograms; and b) a detector means configured for housing and positioning said mass of mercury, wherein said detector means is adapted for detecting changes in the shape of said mass of mercury from said initial shape due to activity of the patient irrespective of the direction in which forces act relative to the geometry of the sensor, and generating a signal indicative of said change, so that when a force in a direction is applied to said mass of mercury said detector means detects said change in shape from said initial shape as a result and in the direction of said applied force and said detector means generates said signal indicative of said change thereby detecting the activity of the patient.

2. The sensor of claim 1, wherein said container is spherical.

3. The sensor of claim 1, wherein said container is hemispherical.

4. The sensor of claim 1, wherein said container is cylindrical.

5. The sensor of claim 1, further comprising an electrically insulated container for housing said mass of mercury, and wherein said detector means comprises two electrically conductive elements for projecting into said container and for contacting said mass of mercury so that when a force is applied to said mass of mercury, said detector means detects variable changes in said predetermined shape of said mass of mercury as a result of said applied force and said detector means generates a continuously variable signal indicative of said variable change.

6. The sensor of claim 1, further comprising an electrically conductive container for housing said mass of mercury, wherein said detector means further comprises an at least partially electrically conductive element insulated from said container, and wherein said element contacts said mass of mercury so that said mass of mercury contacts said element and said container so that when a force is applied to said mass of mercury, said detector means continually detects variable changes in said predetermined shape of said mass of mercury as a result of said applied force and said detector means generates a continuously variable signal indicative of said variable change.

7. The sensor of claim 6, wherein said element is a resistive element so that the sensor is adapted to detect changes in electrical resistance between said mass of mercury and said resistive element so that said variable change represents a variable area of contact between said mass of mercury and said resistive element.

8. The sensor of claims 3 or 4, further comprising a second sensor wherein said second sensor is identical to said sensor, wherein said containers of said each said sensor face one another.

9. The sensor of claim 1, wherein said detector means detects vertical changes in said initial shape of said mass of mercury.

10. The sensor of claim 9, wherein said mass of mercury is about 30 micrograms.

* * * * *